US009671262B2

(12) United States Patent
Ljungdahl et al.

(10) Patent No.: US 9,671,262 B2
(45) Date of Patent: Jun. 6, 2017

(54) SYSTEMS AND METHODS FOR ANALYZING FLOWBACK COMPOSITIONS IN REAL TIME

(71) Applicant: Halliburton Energy Services, Inc., Houston, TX (US)

(72) Inventors: Patrick Matthew Ljungdahl, Houston, TX (US); Sean A. Roach, Houston, TX (US); Alexis Wachtel, II, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 266 days.

(21) Appl. No.: 14/328,198

(22) Filed: Jul. 10, 2014

(65) Prior Publication Data

US 2014/0324366 A1    Oct. 30, 2014

Related U.S. Application Data

(62) Division of application No. 13/664,732, filed on Oct. 31, 2012, now Pat. No. 8,812,238.

(51) Int. Cl.
*G01F 1/66* (2006.01)
*E21B 47/00* (2012.01)
(Continued)

(52) U.S. Cl.
CPC ............ *G01F 1/661* (2013.01); *E21B 21/067* (2013.01); *E21B 47/00* (2013.01); *E21B 49/005* (2013.01);
(Continued)

(58) Field of Classification Search
CPC ................. G01F 1/86; G01F 1/00; G01F 1/76
(Continued)

(56) References Cited

U.S. PATENT DOCUMENTS

| 4,403,146 A |   | 9/1983 | Neufeld |         |
|-------------|---|--------|---------|---------|
| 5,099,697 A | * | 3/1992 | Agar    | G01F 1/74 |
|             |   |        |         | 73/195   |

(Continued)

FOREIGN PATENT DOCUMENTS

| WO | 98/37307 A1   | 8/1998 |
|----|---------------|--------|
| WO | 2014070905 A1 | 5/2014 |

OTHER PUBLICATIONS

Baldauff et al., "Profiling and Quantifying Complex Multiphase Flow", 2004, Oilfied Review, pp. 4-13.*

(Continued)

*Primary Examiner* — Mischita Henson
(74) *Attorney, Agent, or Firm* — McDermott Will & Emery LLP

(57) ABSTRACT

An example system includes a separator that accepts and separates a multiphase flowback effluent stream into a plurality of secondary streams. A first sensor assembly monitors the multiphase flowback effluent stream and generates a first signal corresponding to at least one characteristic of the multiphase flowback effluent stream. A second sensor assembly monitors one of the plurality of secondary streams and generates a second signal corresponding to at least one characteristic of the one of the plurality of secondary streams. A signal processor receives the first and second signals and determines a mass flow rate of a substance present in both the multiphase flowback effluent stream and the one of the plurality of secondary streams.

20 Claims, 4 Drawing Sheets

(51) Int. Cl.
*G01F 1/86* (2006.01)
*E21B 49/00* (2006.01)
*E21B 21/06* (2006.01)
*E21B 49/08* (2006.01)
*G01F 1/708* (2006.01)
*G01F 1/74* (2006.01)
*G01N 21/31* (2006.01)

(52) U.S. Cl.
CPC ............ *E21B 49/08* (2013.01); *G01F 1/7086* (2013.01); *G01F 1/74* (2013.01); *G01F 1/86* (2013.01); *G01N 21/31* (2013.01)

(58) Field of Classification Search
USPC .................................................. 702/6, 12, 50
See application file for complete search history.

(56) References Cited

U.S. PATENT DOCUMENTS

| | | | |
|---|---|---|---|
| 5,678,643 A | 10/1997 | Robbins et al. | |
| 5,680,899 A * | 10/1997 | Waid | E21B 43/12 166/250.01 |
| 6,198,531 B1 * | 3/2001 | Myrick | G01J 3/28 356/213 |
| 6,529,276 B1 | 3/2003 | Myrick | |
| 6,561,041 B1 * | 5/2003 | Eck | E21B 47/10 73/861.04 |
| 7,123,844 B2 | 10/2006 | Myrick | |
| 7,697,141 B2 | 4/2010 | Jones et al. | |
| 7,834,999 B2 | 11/2010 | Myrick et al. | |
| 7,911,605 B2 | 3/2011 | Myrick et al. | |
| 7,920,258 B2 * | 4/2011 | Myrick | G01J 3/02 356/300 |
| 8,049,881 B2 | 11/2011 | Myrick et al. | |
| 8,208,147 B2 | 6/2012 | Myrick et al. | |
| 8,358,418 B2 | 1/2013 | Myrick et al. | |
| 9,103,716 B2 * | 8/2015 | Tunheim | G01J 3/0264 |
| 2004/0011140 A1 | 1/2004 | Coulthard et al. | |
| 2005/0016292 A1 | 1/2005 | Dutton et al. | |
| 2008/0154535 A1 | 6/2008 | Sparks et al. | |
| 2009/0182693 A1 | 7/2009 | Fulton et al. | |
| 2011/0111507 A1 | 5/2011 | Jiang et al. | |
| 2012/0000643 A1 | 1/2012 | Bruun et al. | |
| 2012/0084021 A1 * | 4/2012 | Jones | E21B 47/10 702/45 |
| 2012/0150451 A1 | 6/2012 | Skinner et al. | |
| 2013/0014940 A1 * | 1/2013 | Fripp | E21B 43/2406 166/250.06 |
| 2013/0032344 A1 * | 2/2013 | Freese | E21B 43/16 166/279 |

OTHER PUBLICATIONS

Afanasyev et al., "Multiphase Fluid Samples: A Critical Piece of the Puzzle", 2009, Oilfied Review, vol. 21 No. 2, pp. 30-37.*

Muhammad Munir et al., "Cross Correlation Velocity Measurement of Multiphase Flow", Feb. 2015, International Journal of Science and Research (IJSR), vol. 4 Issue 2, Paper ID: SUB151217, pp. 802-807.*

César Yutaka Ofuchi et al., "Extended Autocorrelation Velocity Estimator Applied to Fluid Engineering", Aug. 27-29, 2014, 9th International Symposium on Ultrasonic Doppler Methods for Fluid Mechanics and Fluid Engineering, pp. 109-112.*

International Search Report and Written Opinion for PCT/US2013/067526 dated Feb. 12, 2014.

* cited by examiner

SYSTEMS AND METHODS FOR ANALYZING FLOWBACK COMPOSITIONS IN REAL TIME

CROSS-REFERENCE TO RELATED APPLICATIONS

The present application is a division of and claims priority to U.S. application Ser. No. 13/664,732, which was filed on Oct. 31, 2012.

BACKGROUND

The present invention relates to the separation of a flowback effluent stream and, in particular, to systems and methods for the real-time analysis of the composition of an input flowback effluent stream or one or more separated output effluent streams.

Flowback is the discharge of an effluent stream of mixed materials that is generated during a remedial operation directed, for example, toward well completion or fracture stimulation. The flowback effluent stream may contain one or more of water, liquid hydrocarbons, chemical additives, cuttings, abrasives, proppants, suspended solids, emulsions, and entrained gases. Disposal of this effluent stream may be difficult and costly, depending on the particular composition of the effluent stream, in light of environmental regulations and responsible corporate behavior. With the increased use of hydraulic fracturing to increase the productivity of certain reservoirs, future environmental regulatory requirements may require an accounting of the amount of chemicals introduced into a wellbore as well as the amount removed in an effluent stream in a hydraulic fracturing operation.

Most hydrocarbon-bearing reservoirs produce a mixture of oil and/or gas together with water, usually in the form of brine, and large amounts of dissolved minerals or precipitates, mostly common salts. In fact, in some oil wells, water and other by-products can amount to as much as eighty to ninety percent of the total production yield. This is particularly true during the later stages of production. Somewhere in the production process the produced mixture undergoes a separation process where the oil/gas is separated from the remaining components of the mixture and subsequently delivered to a refinery for treatment. The water and remaining components are usually removed from the hydrocarbons using one or more single phase or multi-phase separation devices. Generally, these devices operate to agglomerate and coalesce the produced hydrocarbons, thereby separating them from the water and other components of the produced mixture. Similar separation processes may be used to process a flowback effluent stream.

In some production and flowback cases, the separated water and other components are able to be pumped back into the ground, perhaps in some borehole neighboring the one from which it was removed. This process simply replaces a portion of the liquid removed from the reservoir, but also simultaneously serves to maintain required formation pressures for efficient production rates. In offshore applications, it is often desirable to discharge the produced water directly into the surrounding ocean, thereby eliminating the expense of pumping the fluid back downhole.

Before the water can be discharged into the ocean, however, or any other body of water (e.g., rivers, lakes, streams, etc. in other applications) it must first be rigorously tested to make sure that it does not contain any oil or other impurities that could damage the surrounding sea life. As environmental regulations increasingly become more stringent with respect to the disposal of produced water into the ocean, it becomes increasingly crucial to obtain accurate and timely analysis of the separated fluids to ensure compliance with the regulations.

SUMMARY OF THE INVENTION

The present invention relates to the separation of a flowback effluent stream and, in particular, to systems and methods for the real-time analysis of the composition of an input flowback effluent stream or one or more separated output effluent streams.

In some embodiments, a system is disclosed and may include a separator configured to accept and separate a multiphase flowback effluent stream into a plurality of secondary streams, a first sensor assembly arranged to monitor the flowback effluent stream and generate a first signal corresponding to at least one characteristic of the flowback effluent stream, the first sensor assembly including a first optical computing device having an integrated computational element (ICE) configured to optically interact with the flowback effluent stream, a second sensor assembly arranged to monitor one of the plurality of secondary streams and generate a second signal corresponding to at least one characteristic of the one of the plurality of secondary streams, the second sensor assembly including a second optical computing device having an ICE configured to optically interact with the one of the plurality of secondary streams, and a signal processor configured to receive the first and second signals and determine a mass flow rate of a substance present in both the flowback effluent stream and the one of the plurality of secondary streams.

In other embodiments, a sensor assembly is disclosed. The sensor assembly may include an optical computing device having an integrated computational element (ICE) configured to optically interact with a fluid stream and detect a first characteristic of a substance within the fluid stream, the optical computing device being configured to generate a first signal corresponding to the first characteristic, a parameter sensor configured to measure a second characteristic of the fluid stream and generate a second signal corresponding to the second characteristic, and a processor communicatively coupled to the optical computing device and the parameter sensor, the processor being configured to receive the first and second signals and determine a mass flow rate of the substance.

In yet other embodiments, a method is disclosed that may include determining a concentration of a substance in a flow of a fluid with an optical computing device including at least one integrated computational element (ICE) configured to optically interact with the fluid, determining a mass flow rate of the flow of the fluid, and determining a mass flow rate of the substance.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
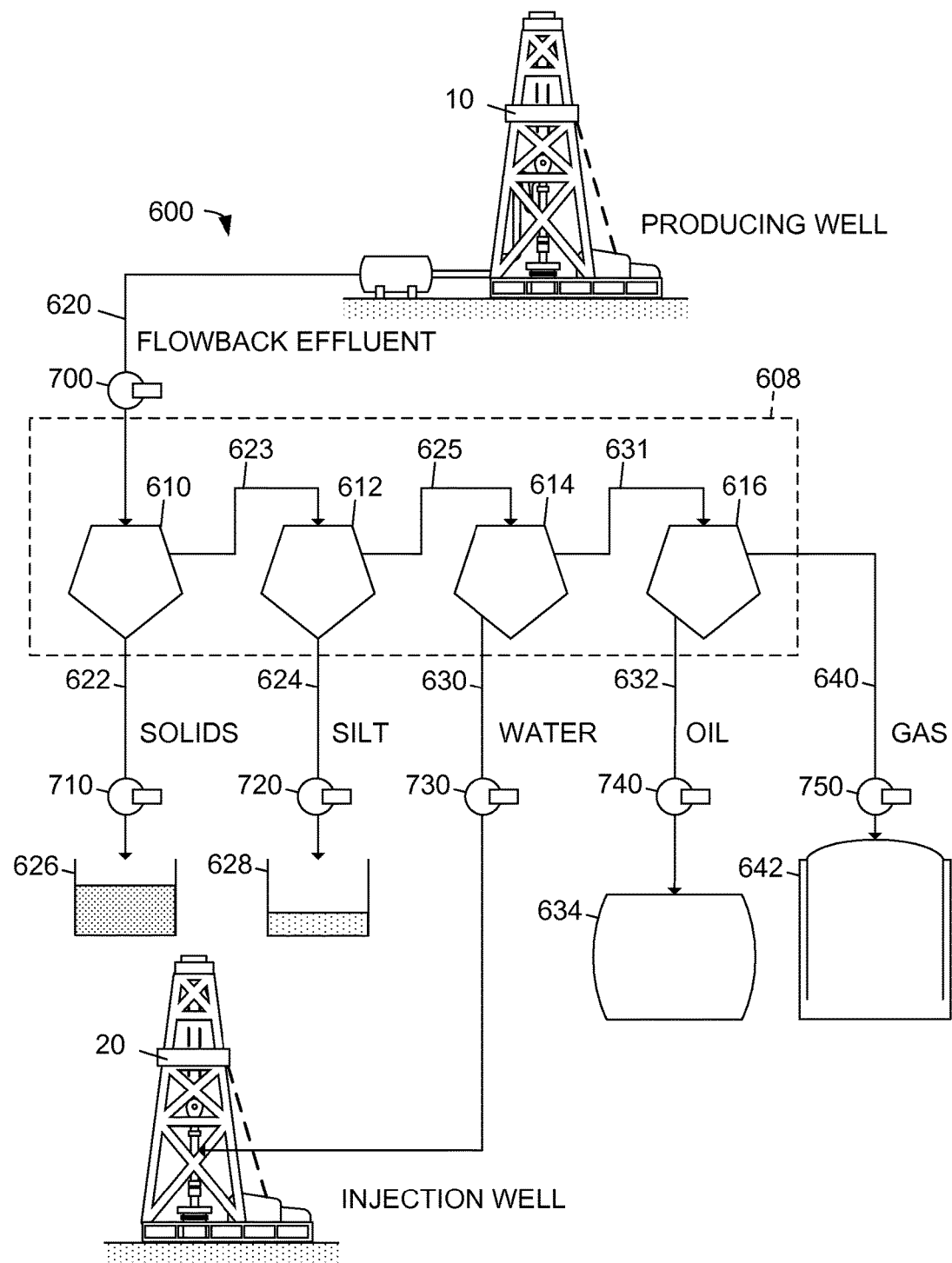
FIG. 1 depicts an exemplary system for the real-time analysis and separation of a flowback effluent, according to one or more embodiments.

The present invention relates to the separation of a flowback effluent stream and, in particular, to systems and methods for the real-time analysis of the composition of an input flowback effluent stream or one or more separated output streams.

Separating a flowback effluent stream into secondary streams, for example, a stream of liquid hydrocarbons or a stream of gaseous hydrocarbons, presents an opportunity to market and sell one or more of these secondary streams. Accordingly, it may be advantageous to determine the composition of a particular secondary stream, for example to verify that there is a minimum purity or "quality" of the hydrocarbon content or to determine a price for the delivered secondary stream. It may also be advantageous to provide quantitative measurements of the amount of certain materials in a secondary stream, for example the amount of hydrocarbon remaining in a secondary stream of water, to verify compliance with regulatory requirements. Continuous monitoring of the composition of the multiple secondary streams exiting a separator may also allow real-time verification of the performance of the separation process.

The exemplary systems and methods described herein employ various configurations of optical computing devices, also commonly referred to as "opticoanalytical devices," for the real-time or near real-time monitoring of fluids. In operation, the systems and methods disclosed herein may be useful and otherwise advantageous in determining the quality of a fluid in fluid separation processes. For example, the optical computing devices disclosed herein, which are described in more detail below, can advantageously provide real-time or near real-time monitoring of fluid separation processes that cannot presently be achieved with either onsite analyses at a job site or via more detailed analyses that take place in a laboratory. With real-time or near real-time analyses on hand, the systems and methods described herein may be able to provide some measure of proactive or responsive control over the fluid separation processes, enable the collection and archival of fluid information in conjunction with operational information to optimize subsequent operations, and/or enhance the capacity for remote job execution.

Those skilled in the art will readily appreciate that the systems and methods disclosed herein may be suitable for use in the oil and gas industry since the described optical computing devices provide a cost-effective, rugged, and accurate means for monitoring hydrocarbon quality in order to facilitate the efficient management of oil/gas production.

It will be appreciated, however, that the various disclosed systems and methods are equally applicable to other technology fields including, but not limited to, the food and drug industry, industrial applications, mining industries, or any field where it may be advantageous to determine the real-time concentration or characteristic of a specific substance in a flowing fluid, especially in separation applications. In at least one embodiment, for example, the present systems and methods may be employed to monitor the quality of potable water after the water has undergone one or more separation processes to remove contaminants or adulterants therefrom. In other embodiments, the present systems and methods may be employed in the military or security fields, such as in submarines or other water craft. In yet other embodiments, the present systems and methods may prove useful in the trucking and auto industries.

The optical computing devices suitable for use in the present embodiments can be deployed at two or more fluidly communicable points within a flow path, such as a fluid separation device or separator. In some embodiments, for example, the optical computing devices may be employed at both inlet and discharge locations of a fluid separator in order to monitor the incoming and outgoing fluids and, therefore, the overall effectiveness of the separator device. In operation, the optical computing device arranged at the discharge location may be configured to ensure a proper or environmentally safe chemical composition of the fluid upon its discharge from the separator. Depending on the location of other optical computing devices, various types of information about the fluid can be obtained. In some cases, for instance, the optical computing devices can be used to monitor changes to the fluid as a result of adding a treatment substance thereto, removing a treatment substance therefrom in a separator, or exposing the fluid to a condition that potentially changes a characteristic of the fluid in some way.

As used herein, the term "oil" refers to a liquid mixture that is composed primarily of hydrocarbons. Oil may include residual amounts of liquid non-hydrocarbon materials and/or dissolved gases.

As used herein, the term "water" refers to a liquid mixture that is composed primarily of $H_2O$. Water may include residual amounts of liquid hydrocarbons and/or dissolved gases.

As used herein, the term "gas" refers to a mixture of one or more materials in gas-phase form, with the primary component being a gaseous hydrocarbon such as methane.

As used herein, the term "silt" refers to solid particles of a size that the particles tend to remain in suspension during conventional separation processes.

Within this document, the term "solids" refers to solid particles of a size that the particles tend to drop out of suspension during conventional separation processes.

As used herein, the term "fluid" refers to any substance that is capable of flowing, including particulate solids, liquids, gases, slurries, emulsions, powders, muds, glasses, mixtures, combinations thereof, and the like. The fluid may be a single phase or a multiphase fluid. In some embodiments, the fluid can be an aqueous fluid, including water or the like. In other embodiments, the fluid may be a non-aqueous fluid, including organic compounds, more specifically, hydrocarbons, oil, a refined component of oil, petrochemical products, and the like. In some embodiments, the fluid can be a treatment fluid or a formation fluid as used in the oil and gas industry. The fluid may also have one or more solids or solid particulate substances entrained therein. For instance, fluids can include various flowable mixtures of solids, liquids and/or gases. Illustrative gases that can be considered fluids according to the present embodiments, include, for example, air, nitrogen, carbon dioxide, argon, helium, methane, ethane, butane, and other hydrocarbon gases, combinations thereof, and/or the like.

As used herein, the term "characteristic" refers to a chemical, mechanical, or physical property of a substance or fluid, such as a flowback effluent. A characteristic may also refer to a chemical, mechanical, or physical property of a phase of a substance or fluid. Illustrative characteristics of a substance and/or a phase of the substance that can be detected or otherwise monitored with the optical computing devices disclosed herein can include, for example, chemical composition (e.g., identity and concentration in total or of individual components), phase presence and concentration, impurity content, pH, viscosity, density, ionic strength, total dissolved solids, salt content, porosity, opacity, bacteria content, combinations thereof, state of matter (i.e., solid, liquid, gas, emulsion, mixtures, etc.), and the like. Exemplary characteristics of a phase of a substance, such as a fluid, can include a volumetric flow rate of the phase, a mass flow rate of the phase, or other properties of the phase derivable from the volumetric and/or mass flow rate. Such properties can be determined for each phase detected in the substance or fluid. Moreover, the phrase "characteristic of interest of/in a fluid" may be used herein to refer to the characteristic of a substance or a phase of the substance contained in or otherwise flowing with the fluid.

As used herein, the term "flow path" refers to a route through which a fluid is capable of being transported between two points. In some cases, the flow path need not be continuous or otherwise contiguous between the two points. Exemplary flow paths include, but are not limited to, a flowline, a pipeline, a production tubular or tubing, an annulus defined between a wellbore and a pipeline, a hose, a process facility, a storage vessel, a separator, a tanker, a railway tank car, a transport ship or vessel, a trough, a stream, a sewer, a subterranean formation, combinations thereof, or the like. In cases where the flow path is a pipeline, or the like, the pipeline may be a pre-commissioned pipeline or an operational pipeline. In other cases, the flow path may be created or generated via movement of an optical computing device through a fluid (e.g., an open air sensor). In yet other cases, the flow path is not necessarily contained within any rigid structure, but refers to the path fluid takes between two points, such as where a fluid flows from one location to another without being contained, per se. It should be noted that the term "flow path" does not necessarily imply that a fluid is flowing therein, rather that a fluid is capable of being transported or otherwise flowable therethrough.

As used herein, the term "phase" refers generally to a state of matter of a substance or material. Exemplary phases include a solid, a liquid (aqueous), a gas, or a plasma, but may also include solid particulates or materials entrained or otherwise dissolved within the liquid or gas phases. The term "phase," however, does not necessarily imply or otherwise refer solely to state of matter, since matter can exist in different phases at the same state of matter. Instead, phase may also refer to a sufficiently homogeneous or continuous geographical region of a substance or material that exhibits a definable border or separation point with respect to other adjacent homogeneous geographical regions. In other words, a phase is a physically distinctive form of matter characterized by having relatively uniform chemical and physical properties. For example, two or more phases may exist in a purely liquid or fluid state of matter, such as a liquid/liquid or gas/gas system. Moreover, mixtures can exist in multiple phases, such as an oil phase and an aqueous phase, or a gas saturated or otherwise dissolved within an oil or an aqueous phase. Further, a gas phase may have oil and water phases dispersed therein as fine globules. In thermodynamically unstable systems, phase may further refer to an emulsion or other finely divided solids trapped in either an oil or aqueous phase.

As used herein, the term "substance," or variations thereof, refers to at least a portion of a material of interest to be evaluated using the optical computing devices described herein. In some embodiments, the substance is the characteristic of interest, as defined above, and may include any integral component or chemical constituent of the fluid flowing within the flow path. In other embodiments, the substance may be a material of interest flowing jointly with and otherwise separate from the fluid.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a fluid, or a phase of the fluid, and produce an output of electromagnetic radiation from a processing element arranged within the optical computing device. The processing element may be, for example, an integrated computational element (ICE) used in the optical computing device. The electromagnetic radiation that optically interacts with the processing element is changed so as to be readable by a detector, such that an output of the detector can be correlated to a characteristic of the fluid or a phase of the fluid. The output of electromagnetic radiation from the processing element can be reflected electromagnetic radiation, transmitted electromagnetic radiation, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid or a phase thereof, for example via fluorescence, luminescence, Raman, Mie, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements), a fluid, or a phase of the fluid. Accordingly, optically interacted light refers to electromagnetic radiation that has been reflected, transmitted, scattered, diffracted, or absorbed by, emitted, or re-radiated, for example, using an integrated computational element, but may also apply to interaction with a fluid or a phase of the fluid.

The exemplary systems and methods described herein may include at least one optical computing device arranged along or in a flow path in order to monitor a fluid flowing or otherwise contained therein. Each optical computing device may include an electromagnetic radiation source, at least one processing element (e.g., an integrated computational element), and at least one detector arranged to receive optically interacted light from the at least one processing element or the fluid. In some embodiments, the exemplary optical computing devices may be specifically configured for detecting, analyzing, and quantitatively measuring a particular characteristic of interest of the fluid or a phase of the fluid in the flow path. In other embodiments, the optical computing devices may be general purpose optical devices, with post-acquisition processing (e.g., through computer means) being used to specifically detect the characteristic of the fluid or phase of the fluid.

In some embodiments, suitable structural components for the exemplary optical computing devices are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments or uses disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically designed to detect and analyze particular characteristics of interest of a fluid or a phase of the fluid. As a result, interfering signals are discriminated from those of interest in the fluid by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic being monitored in the fluid.

The optical computing devices may be configured to detect as many characteristics of interest as desired in the fluid. All that is required to accomplish the monitoring of multiple characteristics is the incorporation of suitable processing and detection means within the optical computing device for each characteristic of interest. In some embodiments, the properties of the characteristic can be a combination of the properties of two or more analytes present therein (e.g., a linear, non-linear, logarithmic, and/or exponential combination). Accordingly, the more characteristics and analytes that are detected and analyzed using the optical computing devices, the more accurately the properties of the given fluid or phase of the fluid will be determined.

The optical computing devices described herein utilize electromagnetic radiation to perform calculations, as opposed to the hardwired circuits of conventional electronic processors or sensors. When electromagnetic radiation interacts with a fluid, unique physical and chemical information about the fluid or a phase within the fluid may be encoded in the electromagnetic radiation that is reflected from, transmitted through, or radiated from the fluid. This information is often referred to as the spectral "fingerprint" of the fluid. The optical computing devices described herein are capable of extracting the information of the spectral fingerprint of multiple characteristics within a fluid, and converting that information into a detectable output relating to one or more properties of the fluid or a phase within the fluid. That is, through suitable configurations of the optical computing devices, electromagnetic radiation associated with a characteristic of the fluid can be separated from electromagnetic radiation associated with all other components of the fluid in order to estimate the properties of the fluid or a phase within the fluid in real-time or near real-time.

It may be particularly advantageous to utilize one or more of these optical computing devices as part of a sensor assembly configured to monitor one or more characteristics of a flowback effluent stream as it is treated in a separator. In certain embodiments, the optical computing device(s) forming part of the sensor assembly may include an integrated computational element (ICE) configured to monitor a particular characteristic that identifies a substance that is part of the flowback effluent fluid. In certain embodiments, the sensor assembly may also be configured to monitor the flow rate of the flowback effluent stream. In certain embodiments, the sensor assembly include an optical computing device configured to monitor both the characteristic of the substance and the flow rate.

For commercial or regulatory reasons, it may be advantageous to determine the total amount of a secondary stream or of a single substance of one or more of the secondary streams. For example, measurement of a particular chemical may allow the documentation of the total amount of that chemical discharged within a period of time to show compliance with a regulatory requirement. A second example may be the determination of the total quantity of methane delivered to a customer in a secondary gas stream so as to prepare an accurate deliverable pricing for that customer. In certain embodiments, a measurement of a characteristic of a substance and a measurement of a velocity of the flow that contains the substance can be combined to provide a mass flow rate of the particular substance, and monitoring of the characteristic and velocity at least at periodic intervals over a period of time can be combined with the intervals and the total period of time to provide a total delivered mass of the substance.

FIG. 1 depicts an exemplary system 600 for the real-time analysis and separation of a multiphase flowback effluent stream 620 according to certain aspects of the present disclosure. In this example, a flowback effluent stream 620 is received from a producing well 10 where, for example, a fracture stimulation process may be underway. The flowback effluent stream 620 is provided, in this example, to a four-phase, closed-loop separator 608, wherein the "closed-loop" descriptor indicates that the liquid and gas secondary streams 630, 632, 640 are captured rather than released or, in the case of the gas secondary stream, flared off.

While shown in FIG. 1 as a four-phase separator device, those skilled in the art will readily appreciated that the fluid separator 608 may be any type of separator known to those skilled in the art. For example, the illustrated separator 608 may be configured to accept as an input the flowback effluent stream 620 and provide secondary streams 622, 624, 630, 632, and 640 of solids, silt, water, oil, and gas, respectively. In other embodiments, however, the separator 608 may be a three-phase separator configured to separate the flowback effluent stream 620 into water, gas, and oil phases. Those skilled in the art will readily appreciate that other numbers and types of secondary flows may be provided, in certain embodiments, without departing from the scope of the disclosure.

In operation, the separator 608 may be used to separate one or more components in the flowback effluent stream 602 from one or more other components present therein. For example, the fluid separator 608 may include any type of separator used to separate wellbore production fluids into their constituent components of, for example, oil, gas, water, precipitates, impurities, condensates (e.g., BTEX compounds), multiphase fluids, combinations thereof, and the like. Suitable separators may include separators that operate on the principle of density separation or separators that operate on the principle of centrifugal separation. In operation, a higher density material or substance (e.g., water) may be separated from a lower density material or substance (e.g., gas, oil, etc.) via differential settling or centrifuging, as known in the art. In certain embodiments, the separator 608 may comprise, for example and without limitation, oil and gas separators, stage separators, trap separators, knockout vessels (knockout drum, knockout trap, water knockout, or liquid knockout), flash chamber separators (flash vessel or flash trap), expansion separator or expansion vessel, scrubbers (gas scrubber), corrugated plate receptors, filters (gas filter), cyclone technology (gas/solid separation, hydrocyclones for liquid phase separation), and flocculent assisted dissolved air and induced air flotation (DAF, IAF for solid and oil separation for oily waste treatment). A separator 608, in certain embodiments, may have portions configured as vertical or horizontal process flows.

In some embodiments, various treatment chemicals, agents, or substances, as known in the art, may be added to one or more of the secondary streams 620, 623, 625, or 631 to help facilitate a more efficient separation process. In certain embodiments, such treatment substances may include, for example, emulsion breakers, de-foaming agents, digester organisms, coalescing agents, and flocculants. In certain embodiments, the relative concentrations of such treatment substances can be monitored and measured using one or more of the sensor assemblies 700, 710, 720, 730, 740, and 750 described below.

As illustrated, the separator 608 includes a solids separator 610, an oil/water separator 614, and an oil/gas separator 616, thus producing the four output phases of solids, water, oil, and gas, as secondary streams. In certain embodiments, the separator 608 may further include a silt separator 612 configured to remove fine suspended solids that may not have been removed by the initial solids separator 610. The solids separator 610 allows solids that are suspended in the effluent stream 620 to settle out and be removed, for example, as a high-solids slurry in solids secondary stream 622 that is directed into a solids holding tank 626. A cleaned effluent stream 623 is, in at least one embodiment, directed to the silt separator 612 wherein the remaining silt (if any) is filtered out of the effluent stream 623 and removed in a silt secondary stream 624 directed into a silt holding tank 628. In certain embodiments, the silt secondary stream 624 may be directed into the solids holding tank 626. In certain embodiments, the solids separation process is performed in a manifold or other separation process (not shown in FIG. 1) prior to the cleaned effluent stream 623 entering the separator 608.

The filtered effluent stream 625 may be directed to the oil/water separator 614 which may remove the water from the oil and gas and, in at least one embodiment, direct a water secondary stream 630 to an injection well 20 where at least a portion of the water stream 630 may be injected into a subterranean formation, for example. A de-watered effluent stream 631 is directed to the oil/gas separator 616 where the gas is removed from the oil. An oil secondary stream 632 is directed, in this example, to a holding tank 634 and a gas secondary stream 640 is directed, in this example, to a storage tank 642. In certain embodiments, the gas secondary stream 640 may be directed through a mass flow meter and into a pipeline (not shown in FIG. 1) configured to transport the gas secondary stream 640 to a remote location.

In the example system 600, various sensor assemblies 700, 710, 720, 730, 740, and 750 may be coupled to or otherwise arranged within the secondary streams 620, 622, 624, 630, 632, and 640, respectively. In certain embodiments, the system 600 may include a reduced number of sensor assemblies coupled to one or more of the lines for the streams 620, 622, 624, 630, 632, and 640. In certain embodiments, each sensor assembly 700, 710, 720, 730, 740, and 750 may include at least one composition sensor and at least one fluid properties sensor, which are discussed in greater detail below with respect to FIG. 2. In some embodiments, one of more of the sensor assemblies 700, 710, 720, 730, 740, and 750 may have only one composition sensor or fluid properties sensor. In certain embodiments, each sensor assembly 700, 710, 720, 730, 740, and 750 may be configured to detect identical characteristics of the respective effluent flows. In other embodiments, however, one or more of the sensor assemblies 700, 710, 720, 730, 740, and 750 may be different from each other in terms of their sensing capabilities. In certain embodiments, the composition sensors of one or more of the sensor assemblies 700, 710, 720, 730, 740, and 750 may be configured to sense one or more substances in the effluent stream from a particular source, for example the producing well 10.

In certain embodiments, one or more sensor assemblies (not shown in FIG. 1) that are similar to one of the sensor assemblies 700, 710, 720, 730, 740, and 750 may be coupled to one or more of the internal effluent streams 623, 625, and 631. Comparison of the measured characteristics of an internal effluent stream that is immediately upstream of a separation process, for example the filtered effluent stream 625 that is upstream of the oil/water separator 614, to the measured characteristics of the two separated streams, for example the water secondary stream 630 and the de-watered effluent stream 631, may allow improved monitoring of that particular separation process.

In certain embodiments, the oil secondary stream 632 may contain a liquid hydrocarbon that may be sold to a customer. In certain embodiments, the gas secondary stream 640 may contain a gaseous hydrocarbon, for example methane, that may be sold to a customer. One or both of the sensor assemblies 740 and 750 may determine a purity or quality of the respective oil and gas secondary streams 632, 640 and/or a quantity of oil and/or gas delivered, as the price paid by the customer for the oil and/or gas may depend on either the actual condition or verification of a minimum condition of the oil and/or gas.

Figure 2:
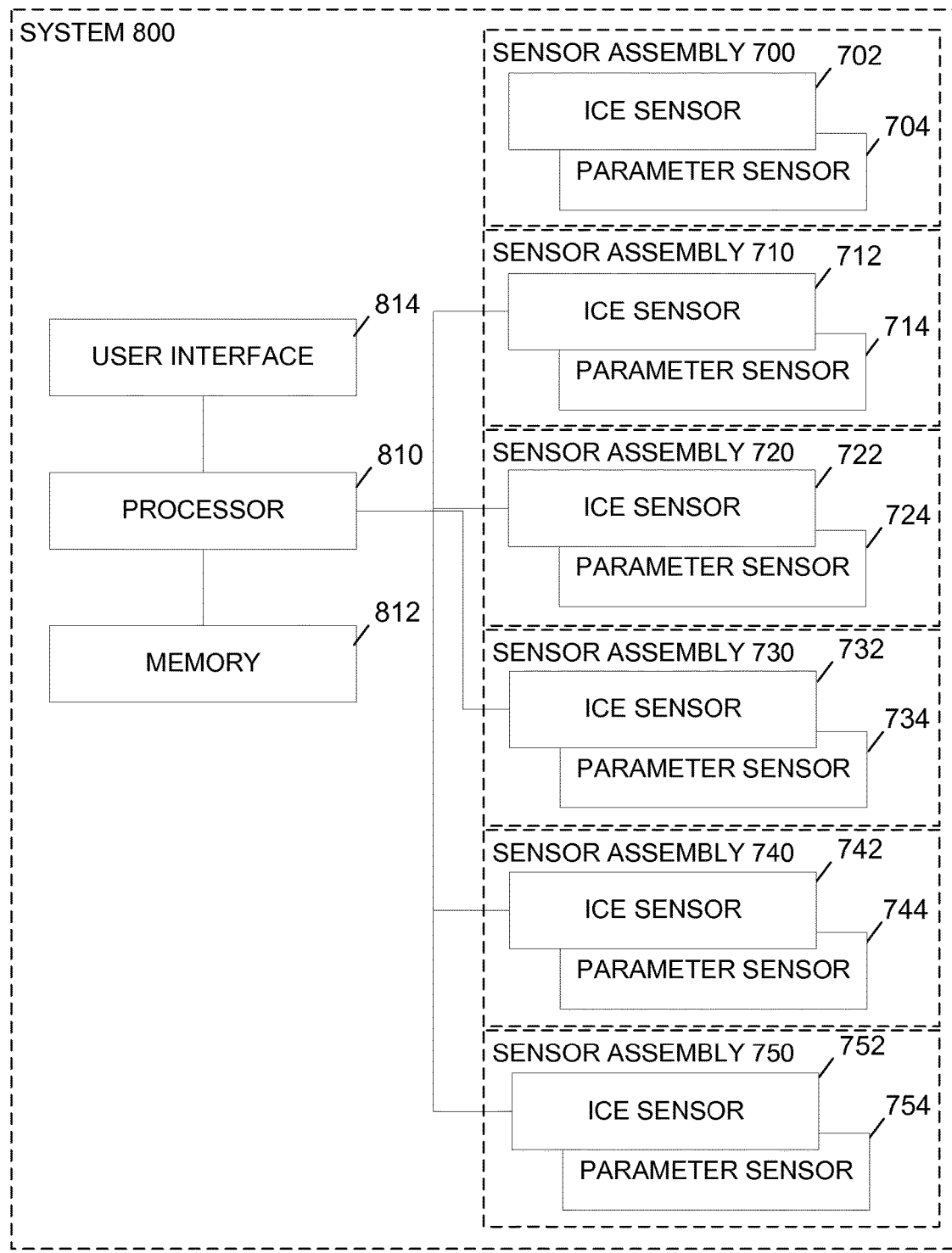
FIG. 2 is a block diagram of an embodiment of an real-time flowback effluent analysis, according to one or more embodiments.

Referring now to FIG. 2, with continued reference to FIG. 1, illustrated is a block diagram of an embodiment of a real-time flowback effluent analysis system 800, according to certain aspects of the present disclosure. The system 800 includes a processor 810 communicatively coupled to a user interface 814 that, in certain embodiments, may include one or more of a display, a printer, a user input device such as a mouse or keyboard, and a communication port to an external system. The processor 810 may also be communicatively coupled to a memory 812 that may be local or remote and is configured to store programs and data. In certain embodiments, the memory 812 may include one or more sequences of instructions, programming stances, or code that configure the processor 810 to perform various operations and functions.

The system 800 may also include the sensor assemblies 700, 710, 720, 730, 740, and 750 of FIG. 1. As illustrated, the sensor assembly 700 may include an ICE sensor 702 and a multiphase fluid parameter sensor 704. As will be discussed in greater detail below, the ICE sensor 702 may be an optical computing device that employs one or more integrated computational elements. In certain embodiments, the ICE sensor 702 may be tuned or otherwise configured to detect one or more characteristics of a substance within the fluid being monitored, for example the flowback effluent stream 620. Flowback effluent streams may include, for example, one or more ions (e.g., monoatomic and/or polyatomic) such as, but not limited to, $HCO_3^-$, $Cl^-$, $SO_4^{2-}$, $Na^+$, $K^+$, $Ca^{2+}$, $Mg^{2+}$, $Ba^{2+}$, $Sr^{2+}$, and $Fe^{3+}$ (total Fe). Other chemical constituents that may be found in the flowback effluent streams may include on or more of hydrochloric acid, muriatic acid, glutaraldehyde, ammonium persulfate, N,n-dimethyl formamide, borate salts, polyacrylamide, mineral oil, citric acid, potassium chloride, ammonium bisulfate, sodium carbonate, potassium carbonate, silica, quartz sand, ethylene glycol, isopropanol, guar gum, hydroethyl cellulose, combinations thereof, and the like. In operation, the ICE sensor 702 may be configured to particularly sense one or more of these substances or chemical constituents. The output of the ICE sensor 702 may comprise a composition of the monitored flow or, in certain embodiments, may include measurements made by the ICE sensor 702 and the determination of the composition may be performed in the processor 810.

The multiphase fluid parameter sensor 704 may be configured, in certain embodiments, to measure one or more characteristics of the flowback effluent stream 620, such as velocity, mass flow rate, and total mass discharge, within a period of time. In certain embodiments, the parameter sensor 704 may comprise a densometer, or the like. In certain embodiments, the parameter sensor 704 may comprise a venture-type sensor. In certain embodiments, the parameter sensor 704 may comprise one or more optical computing devices employing one or more ICE elements configured to detect a characteristic of interest in the fluid and otherwise measure a flow velocity thereof. The combination of information about the percentage composition of one or more substances within the stream, characteristics such as density of the substances, and flow velocity may provide a mass flow rate for one or more of the component substances within the stream being monitored.

As illustrated, each sensor assembly 710, 720, 730, 740, and 750 may include at least one ICE sensor 712, 722, 732, 742, and 752, respectively, and may also include at least one parameter sensor 714, 724, 734, 744, and 754, respectively. In certain embodiments, the ICE sensors 712, 722, 732, 742, and 752 may be configured to detect and measure the same substances as the ICE sensor 702. In other embodiments, the ICE sensors 712, 722, 732, 742, and 752 may be configured to detect and measure only a subset of the substances that are detected by the ICE sensor 702. In yet other embodiments, the ICE sensors 712, 722, 732, 742, and 752 may be configured to detect and measure substances that are not detected by the ICE sensor 702. The processing elements (i.e., integrated computational elements or ICE components) used in the optical computing devices of each ICE sensor 702 may be capable of distinguishing electromagnetic radiation related to the characteristic of interest from electromagnetic radiation related to other components of a fluid.

Figure 3:
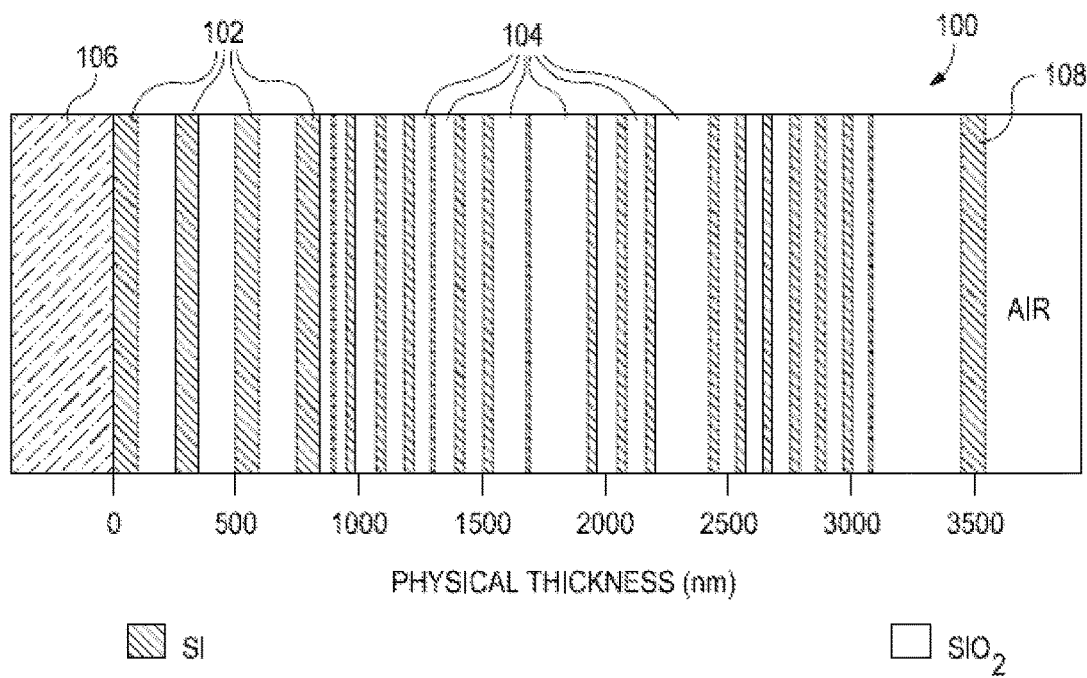
FIG. 3 illustrates an exemplary integrated computation element, according to one or more embodiments.

Referring to FIG. 3, illustrated is an exemplary ICE 100 suitable for use in the optical computing devices used in the sensor assemblies 700, 710, 720, 730, 740, and 750. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 3), the ICE 100 may include a layer 108 that is generally exposed to the environment of the flow path, device, or installation. The number of layers 102, 104 and the thickness of each layer 102, 104 are determined from the spectral attributes acquired from a spectroscopic analysis of a characteristic of the substance using a conventional spectroscopic instrument. The spectrum of interest of a given characteristic of a substance typically includes any number of different wavelengths. It should be understood that the exemplary ICE 100 in FIG. 3 does not, in fact, represent any particular characteristic of a given substance, but is provided for purposes of illustration only. Consequently, the number of layers 102, 104 and their relative thicknesses, as shown in FIG. 3, bear no correlation to any particular characteristic of a given substance. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light processing (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 29, pp. 2876-2893 (1990), which are hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 4:
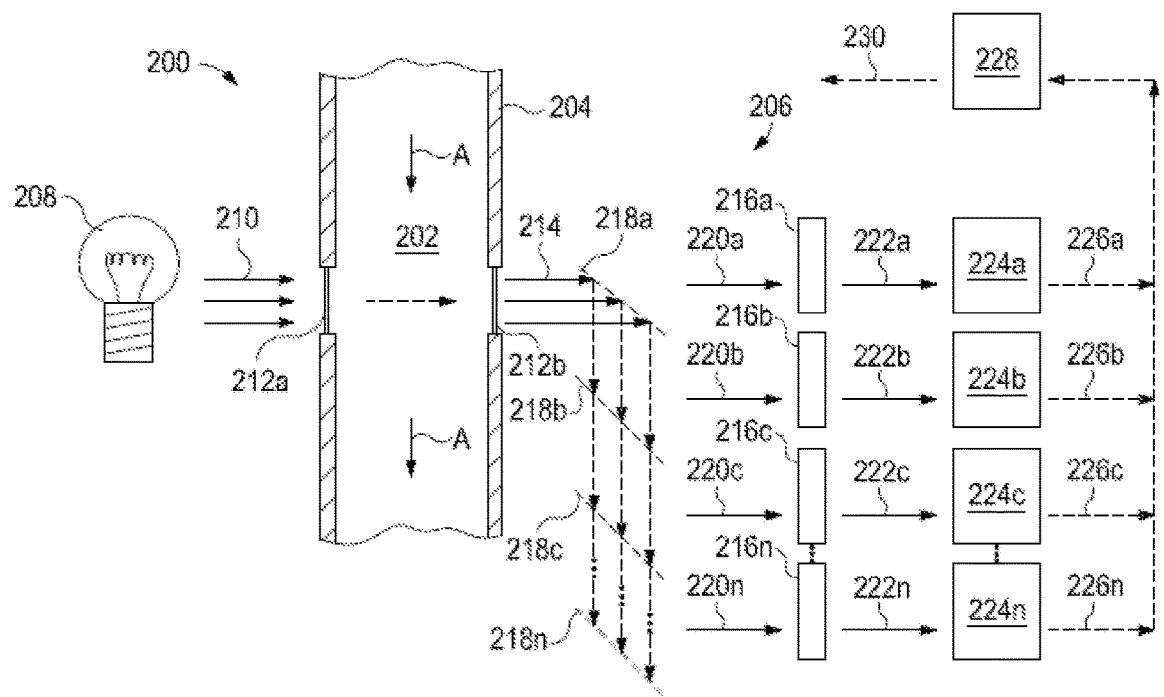
FIG. 4 illustrates an exemplary measurement system for monitoring a fluid present in a flow path, according to one or more embodiments.

Referring now to FIG. 4, illustrated is an exemplary measurement system 200 for monitoring a fluid 202, according to one or more embodiments. In the illustrated embodiment, the fluid 202 may be contained or otherwise flowing within an exemplary flow path 204. The flow path 204 may be a flow line or a pipeline and the fluid 202 present therein may be flowing in the general direction indicated by the arrows A (i.e., from upstream to downstream). In some embodiments, the flow path 204 may be associated with a separator device, such as the four-phase separator 608 of FIG. 1, and the fluid 202 may be the flowback effluent stream 620. As will be appreciated, however, the flow path 204 may be any other type of flow path, as generally described or otherwise defined herein. Portions of the flow path 204 may be arranged substantially vertical, substantially horizontal, or any directional configuration therebetween, without departing from the scope of the disclosure.

The measurement system 200 may include an optical computing device 206 configured to determine a characteristic of interest in the fluid 202 or a phase of the fluid 202 as contained within the flow path 204. In some embodiments, the optical computing device 206 (or variations thereof) may be the optical computing device used in one or more of the sensor assemblies 700, 710, 720, 730, 740, and 750, as described above. As illustrated, the device 206 may include an electromagnetic radiation source 208 configured to emit or otherwise generate electromagnetic radiation 210. The electromagnetic radiation source 208 may be any device capable of emitting or generating electromagnetic radiation, as defined herein. For example, the electromagnetic radiation source 208 may be a light bulb, a light-emitting diode (LED), a laser, a blackbody, a photonic crystal, an x-ray source, combinations thereof, or the like. In some embodiments, a lens (not shown), or any other type of optical device configured to transmit or otherwise convey electromagnetic radiation, may be arranged to collect or otherwise receive the electromagnetic radiation 210 and direct a beam of the same toward the fluid 202.

In one or more embodiments, the optical computing device 206 may be configured to transmit the electromagnetic radiation 210 through the fluid 202 via a first sampling window 212a and a second sampling window 212b arranged radially-opposite the first sampling window 212a on the flow path 204. One or both of the sampling windows 212a,b may be made from a variety of transparent, rigid or semi-rigid materials that are configured to allow transmission of the electromagnetic radiation 210 therethrough. For example, the sampling windows 212a,b may be made of, but is not limited to, glasses, plastics, semi-conductors, sapphires, crystalline materials, polycrystalline materials, hot or cold-pressed powders, combinations thereof, or the like.

As the electromagnetic radiation 210 passes through the fluid 202 via the first and second sampling windows 212a,b, it optically interacts with the fluid 202. Optically interacted radiation 214 is thereby generated and subsequently directed to or otherwise received by one or more ICE 216 arranged within the optical computing device 206, such as a first ICE 216a, a second ICE 216b, a third ICE 216c, and one or more additional ICE 216n. While only four ICE 216a-n are depicted, more or less could be employed, without departing from the scope of the disclosure. As illustrated, the ICE 216a-n may be arranged in parallel within the optical computing device 206 and a series of beam splitters 218a, 218b, 218c, 218n may be used to separate or otherwise redirect the optically interacted radiation 214 such that a respective beam 220a, 220b, 220c, 220n of optically interacted radiation 214 is directed toward a corresponding ICE 216a-n. Those skilled in the art will readily recognize that alternative configurations of the device 206 may allow the optically interacted radiation 214 to be generated by being scattered, diffracted, absorbed, emitted, or re-radiated by and/or from the fluid 202, without departing from the scope of the disclosure.

Each ICE 216a-n may be a spectral component substantially similar to the ICE 100 described above with reference to FIG. 3. Accordingly, in operation each ICE 216a-n may be configured to receive a portion of the optically interacted radiation 214 and produce modified electromagnetic radiation or optically interacted light 222a-n corresponding to a particular characteristic of interest of the fluid 202. As defined above, the optically interacted light 222a-n is electromagnetic radiation that has optically interacted with the ICE 216a-n, whereby an approximate mimicking of the regression vector corresponding to the characteristic of interest of the fluid 202 is obtained.

Each ICE 216a-n may then be configured to transmit its respective optically interacted light 222a-n toward a corresponding detector 224a-n for quantification of the signal. Each detector 224a-n may be any device capable of detecting electromagnetic radiation, and may be generally characterized as an optical transducer. In some embodiments, the detectors 224a-n may be, but are not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

Each detector 224a-n may be configured to produce an output signal in real-time or near real-time in the form of a voltage (or current) that corresponds to the particular characteristic of interest in the fluid 202. For example, each detector 224a-n may generate or otherwise transmit first, second, third, and additional output signals 226a, 226b, 226c, and 226n, respectively. The voltage returned by each detector 224a-n is essentially the dot product of the optical interaction of the optically interacted radiation 214 with the respective ICE 216a-n as a function of the concentration of the characteristic of interest of the fluid 202. As such, each output signal 226a-n produced by its corresponding detector 224a-n and the concentration of the characteristic of interest in the fluid 202 may be related.

The output signals 226a-n may then be received by a signal processor 228 communicably coupled to each detector 224a-n. In certain embodiments, the processor 810 of the flowback effluent analysis system 800 of FIG. 2 may include a signal processor 228. The signal processor 228 may be a computer including a processor and a machine-readable storage medium having instructions stored thereon, which, when executed by the processor, cause the optical computing device 206 to perform a number of operations, such as determining a characteristic of interest of the fluid 202 or a phase of the fluid 202. In real-time or near real-time, the signal processor 228 may be configured to provide a resulting output signal 230 corresponding to one or more characteristics of the fluid 202 or a phase of the fluid 202. In some embodiments, the resulting output signal 230 may be conveyed, either wired or wirelessly, to an operator for consideration. In other embodiments, the resulting output signal 230 may be recognized by the signal processor 228 as being within or without a predetermined or preprogrammed range of suitable operation. If the resulting output signal 230 exceeds the predetermined or preprogrammed range of operation, the signal processor 228 may be configured to alert the operator so appropriate corrective action may be taken, or otherwise autonomously undertake the appropriate corrective action such that the resulting output signal 230 returns to a value within the predetermined or preprogrammed range of operation.

In exemplary operation, each ICE 216a-n may be configured to detect a different characteristic of the fluid 202 or phase of the fluid 202. As a result, each output signal 226a-n may be different, and the resulting output signal 230 may provide an operator with several pieces of valuable data regarding the fluid 202 within the flow path 204. One exemplary characteristic that may be monitored by the device 206 includes the specific states of matter present within the fluid. Another exemplary characteristic that may be determined with the device 206 is the particular phases of the fluid 202 (e.g., water, gas, oil, etc.). For instance, the first ICE 216a may be configured to detect an aqueous phase in the fluid 202, the second ICE 216b may be configured to detect a gas phase in the fluid 202, and the third ICE 216c may be configured to detect an oil phase in the fluid 202. As a result, the device 206 may be able to provide the operator with data regarding which phases are present within the fluid 202 and their respective concentrations. In other embodiments, a single ICE 216a-c may be employed to detect more than one phase characteristic of the fluid 202. For example, one or more of the ICE 216a-c may be used to detect the concentration of methane, and simultaneously determine its state of matter, e.g., gas, solid, liquid, or a mixture/combination thereof.

Other characteristics of the fluid 202 or a phase of the fluid 202 that may be detected with the device 206 include, but are not limited to, salt content, methane concentration, sand or other particulate concentration, hydrogen sulfide ($H_2S$) concentration, scale and/or hydrates (e.g., calcium carbonate) concentration, various ions of interest such as, but not limited to, $Al^+$, $B^+$, $Ba_2^+$, $Sr_2^+$, $Fe^+$, $Fe_2^+$ (or total Fe), $I^+$, $Mn_2^+$, $SO_4^{2-}$, $CO_3^{2-}$, $Ca_2^+$, $Mg_2^+$, $Mn^+$, $Na^+$, $K^+$, $Cl^-$, $Sr^+$, $Zn^+$, sulfates, sulfides, carbonates, oxides, fluid states of matter (e.g., gas, solid, liquid, and mixtures or associated compositions thereof), total dissolved solids, total suspended solids, pH, density, combinations thereof, and the like. Accordingly, the signal processor 228 may be configured to receive the various output signals 226a-n and provide the operator with one or more characteristics of the fluid 202 and/or the phase(s) of the fluid 202 in the form of the resulting output signal 230.

Figure 5:
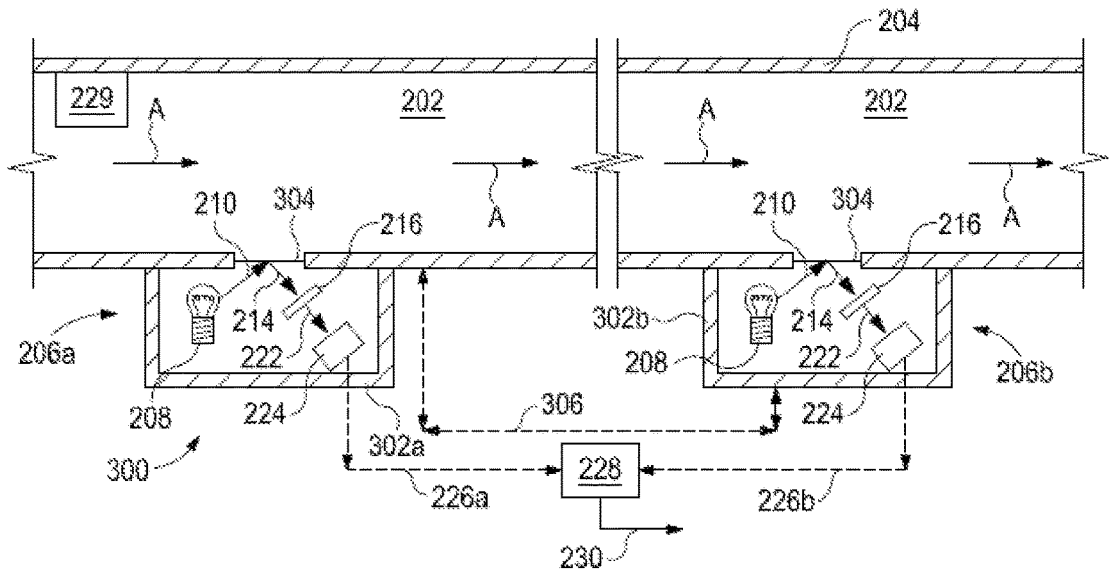
FIG. 5 illustrates another exemplary measurement system for monitoring a fluid present in a flow path, according to one or more embodiments.

Referring now to FIG. 5, with continued reference to FIG. 4, illustrated is another exemplary measurement system 300 for monitoring the fluid 202, according to one or more embodiments. Similar to the measurement system 200 of FIG. 4, the measurement system 300 may be configured to monitor the fluid 202 contained or otherwise flowing within an exemplary flow path 204 and determine a particular characteristic of the fluid 202 within the flow path 204, such as determining a phase or state of matter of the fluid 202, or a concentration of a characteristic or phase that may be present within the fluid 202. Moreover, the measurement system 300, and its described optical computing devices, may be used in conjunction with one or more of the sensor assemblies 700, 710, 720, 730, 740, and 750, as described above.

As illustrated, the measurement system 300 may include at least a first optical computing device 206a and a second optical computing device 206b. The first and second optical computing devices 206a,b may be similar in some respects to the optical computing device 206 of FIG. 4, and therefore may be best understood with reference thereto where like numerals represent like elements not described again in detail. As illustrated, the first and second optical computing devices 206a,b may each be associated with the flow path 204 at independent and distinct monitoring locations along the length thereof. Specifically, the first optical computing device 206a may be located at a first monitoring location and the second optical computing device 206b may be located at a second monitoring location, where the first monitoring location fluidly communicates with the second monitoring location via contiguous portions of the flow path 204.

In some embodiments, the second optical computing device 206b is arranged at a predetermined distance from the first optical computing device 206a along the length of the flow path 204. In other embodiments, however, the first optical computing device 206a may be randomly spaced from the second optical computing device 206b, without departing from the scope of the disclosure. Moreover, while two optical computing devices 206a,b are shown in FIG. 5, it will be appreciated that the measurement system 300 may employ any number of optical computing devices (including one) within the flow path 204 and equally determine the characteristic of the fluid 202 or a phase of the fluid 202. In such embodiments, each additional optical computing device may be spaced from the first and second optical computing devices 206a,b at predetermined or random distances, depending on the application.

Each device 206a,b may be housed within an individual casing or housing coupled or otherwise attached to the flow path 204 at its respective location. As illustrated, for example, the first device 206a may be housed within a first housing 302a and the second device 206b may be housed within a second housing 302b.

In some embodiments, each device 206a,b may include the electromagnetic radiation source 208 configured to emit or otherwise generate electromagnetic radiation 210. In one or more embodiments, each device 206a,b may also include a sampling window 304 arranged adjacent the fluid 202 for detection purposes. The sampling window 304 may be similar to the sampling windows 212a,b of FIG. 4 and made from a variety of transparent, rigid or semi-rigid materials that are configured to allow transmission of the electromagnetic radiation 210 therethrough. After passing through the sampling window 304, the electromagnetic radiation 210 impinges upon and optically interacts with the fluid 202. As a result, optically interacted radiation 214 is generated by and otherwise reflected from the fluid 202. Those skilled in the art, however, will readily recognize that alternative variations of the devices 206a,b may allow the optically interacted radiation 214 to be generated by being transmitted through, scattered, diffracted, absorbed, emitted, or re-radiated (e.g., via fluorescence or phosphorescence methods) by and/or from the fluid 202, without departing from the scope of the disclosure.

The optically interacted radiation 214 of each device 206a,b may be directed to or otherwise be received by an ICE 216 arranged within each corresponding device 206a,b.

Each ICE 216 may be configured to receive the optically interacted radiation 214 and produce modified electromagnetic radiation or optically interacted light 222 corresponding to a particular characteristic of interest of the fluid 202 or a phase of the fluid 202.

It should be noted that, while FIG. 5 depicts the ICE 216 as receiving reflected electromagnetic radiation from the fluid 202, the ICE 216 may be arranged at any point along the optical train of the device 206a,b, without departing from the scope of the disclosure. For example, in one or more embodiments, the ICE 216 may be arranged within the optical train prior to the sampling window 304 and the optical computing device 206a,b will obtain substantially the same results. In other embodiments, the sampling window 304 may serve a dual purpose as both a transmission window and the ICE 216 (i.e., a spectral component). In yet other embodiments, the ICE 216 may generate the optically interacted radiation 222 through reflection, instead of transmission therethrough.

Moreover, while only one ICE 216 is shown in each corresponding device 206a,b, similar to the optical computing device 206 of FIG. 4, embodiments are contemplated herein which include the use of two or more ICE 216 in each device 206a,b, each being configured to detect a different characteristic of the fluid 202 or phase of the fluid 202. In some embodiments, it may be desirable to monitor more than one characteristic of the fluid 202 at a time at each location along the flow path 204. In such embodiments, various configurations of multiple ICE 216 can be used in a single optical computing device 206a,b, where each ICE 216 is configured or otherwise designed to detect a particular and/or distinct characteristic of interest in the fluid 202. For example, as illustrated and discussed in FIG. 4, two or more ICE 216 may be arranged in series or parallel within each device 206a,b and each ICE 216 may be configured to detect a different characteristic of the fluid 202, a different phase of the fluid 202, and/or a different characteristic of a phase of the fluid 202. In such embodiments, one or more beam splitters may be used to divert a portion of the electromagnetic radiation being reflected by, emitted from, or transmitted through the fluid 202 and so that it may optically interact with each ICE 216.

The optically interacted light 222 generated by each ICE 216 may subsequently be conveyed to a detector 224 for quantification of the signal. The detector 224 in each device 206a,b may be configured to produce an output signal in real-time or near real-time in the form of a voltage (or current) that corresponds to the particular characteristic of interest in the fluid 202 or a phase of the fluid 202. For example, the detector 224 arranged within the first device 206a may generate a first output signal 226a, and the detector 224 arranged within the second device 206b may generate a second output signal 226b. The output signal 226a,b from each device 206a,b may be conveyed to or otherwise received by the signal processor 228. In some embodiments, the signal processor 228 may be configured to compute or otherwise identify one or more characteristics of interest of the fluid 202. In other embodiments, the signal processor 228 may be configured to compute or otherwise identify one or more phases present within the fluid 202. In yet other embodiments, the signal processor 228 may be configured to compute or otherwise identify one or more characteristics of a phase present within the fluid 202. In at least one embodiment, the first and second output signals 226a,b may be indicative of characteristics of the fluid 202, such as, but not limited to, pH, viscosity, density or specific gravity, and ionic strength, as measured at the first and second monitoring locations, respectively.

In at least one embodiment, the signal processor 228 may be configured to perform an autocorrelation operation on the collected output signals 226a,b in order to determine a characteristic of a phase of the fluid 202. In particular, for example, the autocorrelation operation may be undertaken such that a factor of fluctuation per unit time is matched to each respective phase of the fluid 202. The signal processor 228 may perform a number of operations, such as determining a characteristic of a phase of the fluid 202 based on results from performing the autocorrelation operation. Exemplary characteristics determined based on results from performing the autocorrelation operation include, but are not limited to, a volumetric flow rate of the phase, a mass flow rate of the phase, flow regime (e.g., turbulent or laminar, or combinations thereof) or other characteristics of the phase derivable from the volumetric and/or mass flow rate. The autocorrelation operation on the collected output signals 226a,b may employ one or more techniques such as, but not limited to, time evolved factor analysis, general autocorrelation, coherence and partial coherence methods, multivariate curve resolution, histogram profiling, or other similar evaluation process.

In some embodiments, a fluid stream perturbing device 229 may be operatively arranged within the flow path 204 upstream from the first and second optical computing devices 206a,b. With the autocorrelation operation based on variations or fluctuations in the phases of the fluid 202 over time, phases that are consistent over distance or mildly grading in composition and properties may be insensitive to the autocorrelation technique for determining flow rates of the phases. The fluid stream perturbing device 229 may be configured to inject a perturbation upstream of the optical computing devices 206a,b relative to a phase of the fluid 202, when the phase is flowing without sufficient variation at the respective measuring points absent the perturbation. Those skilled in the art will readily recognize that natural perturbing instances may occur in the flow path 204 such that use of the fluid stream perturbing device 229 may be reduced or eliminated altogether in some embodiments.

The arrangement of the optical computing devices 206a,b and the evaluation of their measurements may be configured to use perturbation(s) that is/are observable by the such devices 206a,b. For instance, a perturbation may be induction of a gas bubble, a change from laminar flow to turbulent flow, or injection of an absorbing or fluorescing dye. A single perturbation most likely affects different phases differently. However, in the case that a perturbation does not affect a given phase at all, multiple perturbations (one for each independent phase) may be induced. Relative perturbations may be induced in the case that an absolute perturbation provides less than sufficient delineating characterization. For instance, two dies may simultaneously be injected in different concentrations to induce a relative optical density ratio between two different optical band centers. Perturbations may also be varied temporally with characteristic frequencies, beats, or cords so as to lock the pattern.

With a known distance between the first and second optical computing devices 206a,b, and/or the perturbation point, the autocorrelation function using the output signals 226a,b may yield a linear velocity for each phase observed within the fluid 202. This autocorrelation function may make use of various algorithms to perform the autocorrelation operation. Such autocorrelation algorithms may include, but are not limited to, time evolved factor analysis, general autocorrelation, multivariate curve resolution, coherence or partial coherence methods, or histogram profiling. Such algorithms can be part of an artificial neural network configured to use the concentration of each detected characteristic in order to evaluate the overall characteristic(s) of the fluid 202. Illustrative but non-limiting artificial neural networks are described in commonly owned U.S. patent application Ser. No. 11/986,763 (U.S. Patent App. Pub. No. 2009/0182693), which is incorporated herein by reference.

It is to be recognized that an artificial neural network can be trained using samples of fluids 202 having known characteristics, phases, concentrations, compositions, and/or properties, and thereby generating a virtual library. As the virtual library available to the artificial neural network becomes larger, the neural network can become more capable of accurately predicting the characteristics of the fluid 202 and any phases present therein. Furthermore, with sufficient training, the artificial neural network can more accurately predict the characteristics of the fluid 202, even in the presence of unknown characteristics or phases.

To convert the linear flow provided by the autocorrelation analysis of the data received from the output signals 226a,b into volumetric flow, the fluid phase cross section can be determined at the location of each optical computing device 206a,b. For instance, an average phase volume, determined for the regions near each optical computing device 206a,b, can be determined using each optical computing device 206a,b. Alternatively, the optical computing devices 206a,b may configured to detect and determine mass flow of each detected phase. Mass flow and volumetric flow may be interconverted with known phase densities (e.g., densities for water, gases, and oils). Alternatively, if mass flow and volumetric flow are determined, then phase densities may be calculated. In addition, phase compressibility may be derived from the optical computing devices 206a,b if located at points of differing pressures within the flow path 204, or from flow velocities correlated over differing pressures, if phase velocities are known.

Accordingly, the autocorrelation operations of the signal processor 228 provide a mechanism to look at variations in the fluid 202 across the optical computing devices 206a,b. As briefly mentioned above, one example of an autocorrelation operation can be realized by applying a time evolved factor analysis where each optical computing device 206a,b can be considered to be a different channel. An auto correlation function provided by the time evolved factor analysis provides a technique designed to match factors with factors of fluctuation across unit time. In such a system, a number of different factors may be determined, for example, two different factors or three different factors, where each factor is equivalent to the number of phases of the fluid 202. The factor fluctuation per unit time can yield a flow rate for these different phases. If the distance between the optical computing devices 206a,b is known, such a flow rate can be calculated as a volumetric flow rate. Moreover, with known densities of the composition of the fluid 202, the factor fluctuation per unit time can yield a flow rate that translates to mass. In such an analysis, the number of optical computing devices 206a,b dispersed throughout the system 300 may be configured such that they are sensitive to the different phases in the fluid 202. As will be appreciated, a combination of optical computing devices 206a,b, which yield enough degrees of freedom to physically provide the data for the different phases, can be used such that each optical computing device 206a,b need not be sensitive to all phases.

In real-time or near real-time, the signal processor 228 may be configured to provide a resulting output signal 230 corresponding to the characteristic of the fluid 202 or a phase of the fluid 202 based on the results from the autocorrelation operation. In some embodiments, the resulting output signal 230 may be conveyed, either wired or wirelessly, to an operator for consideration. In other embodiments, the resulting output signal 230 may be recognized by the signal processor 228 as being within or without a predetermined or preprogrammed range of suitable operation. If the resulting output signal 230 exceeds the predetermined or preprogrammed range of operation, the signal processor 228 may be configured to alert the operator so appropriate corrective action may be taken, or otherwise autonomously undertake the appropriate corrective action such that the resulting output signal 230 returns to a value within the predetermined or preprogrammed range of operation.

Still referring to FIG. 5, in other embodiments, one of the optical computing devices 206a,b may be omitted from the system 300, such as the first optical computing device 206a, and an optical light pipe 306 may be included to facilitate the monitoring and/or detection of the fluid 202 at or near the first monitoring location. In alternative embodiments, it will be appreciated that the second optical computing device 206b may instead be omitted and the optical light pipe 306 may be used to monitor the fluid 202 at or near the second monitoring location, and equally obtain the same results.

The optical light pipe 306 may be a fiber optic lead, probe, or conduit used for the transmission of electromagnetic radiation to/from the second optical computing device 206b. The optical light pipe 306 may communicably couple the second optical computing device 206b to the fluid 202 at or near the first monitoring location. For example, the optical light pipe 306 may be configured to convey electromagnetic radiation from the second optical computing device 206b to the fluid 202 for the purpose of determining the particular characteristic of the fluid 202 or a phase of the fluid 202. The optical light pipe 306 may also be configured to convey optically interacted radiation from the fluid 202 back to the second optical computing device 206b.

In exemplary operation, the second optical computing device 206b may receive optically interacted radiation from the fluid 202 at both the first and second monitoring locations. The detector 224 arranged within the second optical computing device 206b may be configured to time multiplex the dual beams of optically interacted light from the fluid 202 derived from each monitoring location. For example, the optically interacted radiation received via the optical light pipe 306 at the first monitoring location may be directed to or otherwise received by the second optical computing device 206b at a first time T1, and the optically interacted radiation derived at the second monitoring location may be directed to or otherwise received by the second optical computing device 206b at a second time T2, where the first and second times T1, T2 are distinct time periods that do not spatially overlap.

Consequently, the detector 224 receives at least two distinct beams of optically interacted light from the ICE 216 and is able to convey corresponding output signals 226b for the respective beams to the signal processor 228 for processing. The first beam of optically interacted light may indicate a characteristic of the fluid 202 at the first monitoring location, while the second beam of optically interacted light may indicate the characteristic of the fluid 202 at the second monitoring location. By employing one or more autocorrelation operations as discussed herein above, the signal processor 228 may be able to determine particular phase characteristics of the fluid 202, such as volumetric and mass flow rates, flow regimes (e.g., turbulent or laminar, or combinations thereof), or other characteristics of the phase(s) derivable from the volumetric and/or mass flow rate.

Figure 6:
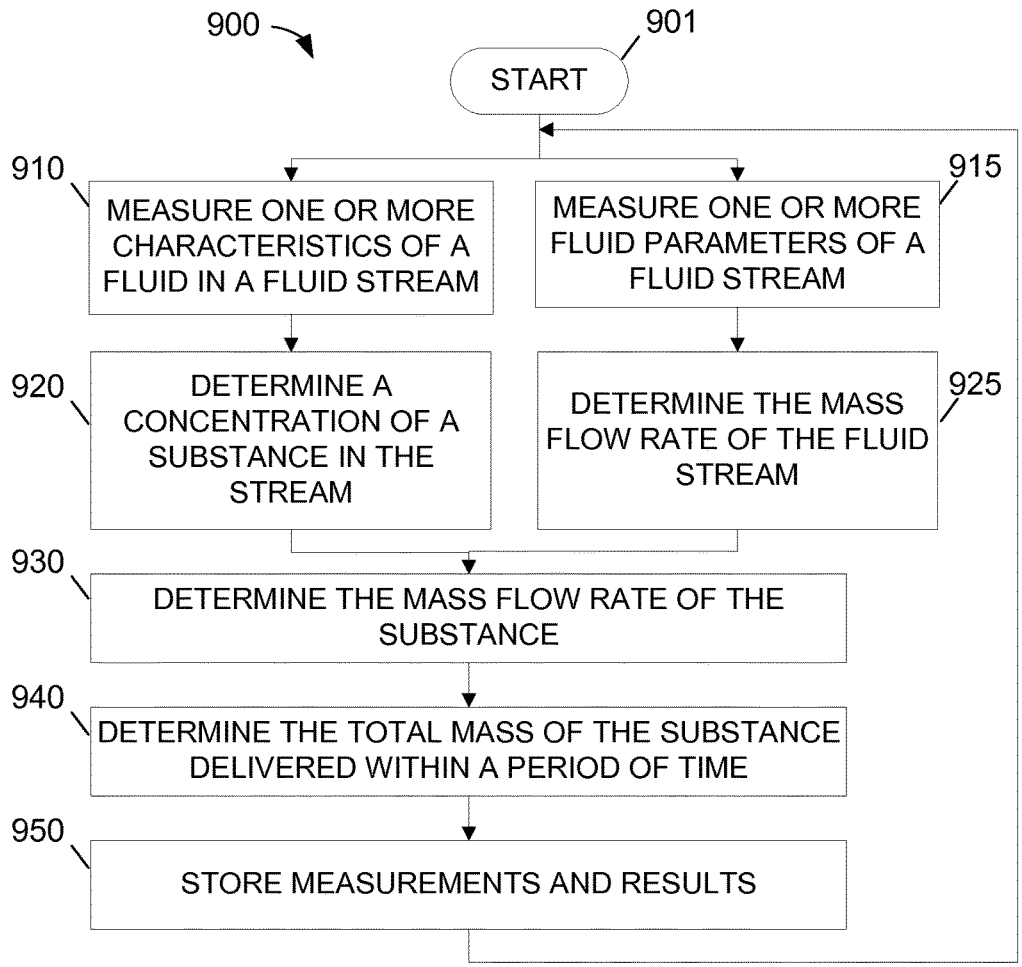
FIG. 6 is a flowchart of an exemplary process for real-time flowback effluent analysis, according to one or more embodiments.

FIG. 6 is a flowchart of an exemplary process 900 for real-time flowback effluent analysis, according to certain aspects of the present disclosure. The process 900 simultaneously measures a characteristic of a fluid stream (e.g., a flowback effluent stream), as at 910, and one or more fluid parameters of the fluid stream, as at 915. In some embodiments, the characteristic of the fluid stream may be measured with a sensor that includes one or more ICE components as used within an optical computing device, as generally described above. The process 900 then proceeds to determine a concentration of a substance in the fluid, as at 920, using the detected characteristic of the fluid stream. In one or more embodiments, the concentration of the substance determined may include a volume percentage of the particular substance.

In certain embodiments, the measurement of the one or more fluid parameters of the fluid stream may include the detection of a characteristic of the fluid. For example, the characteristic of the fluid may be an increase in a concentration of a substance which may be determined using a first ICE at a first time at a first point along the fluid stream. The detection of the same characteristic of the fluid may be determined using a second ICE at a second time at a second point along the fluid stream, where the first and second points are separated by a known distance. In certain embodiments the measurement of the one or more fluid parameters of the fluid stream may further include a determination of a velocity of the fluid stream by dividing the distance between the first and second points by the elapsed time between the first and second times.

The process 900 may further include determining a mass flow rate of the fluid stream, as at 925. In some embodiments, this may be accomplished by multiplying the density of the fluid by the velocity of the fluid. In certain embodiments, the density may also be determined using, for example, a densometer. Once the mass flow rate of the fluid stream and the concentration of the substance in the fluid stream are known, the mass flow rate of the substance may be determined, as at 930, for example by multiplying the mass flow rate of the fluid stream by the concentration of the substance. In certain embodiments, it is desirable to determine the total mass of the substance delivered within a period of time, as at 940. This may be accomplished, for example, by integrating the mass flow rate of the substance over the period of time. This may be beneficial if, for example, one or more of the oil and gas secondary streams 632, 640 of FIG. 1 are being sold and it is determine the amount delivered within a period of time, such as a month. Some or all of the measurements, calculations, and determinations are stored, as at 950, for example, in the memory 812 shown in FIG. 2 or sent to an external memory through the user interface 814.

In summary, the disclosed system and methods of measuring one or more characteristics, such as the concentrations, of one or more substances in a multiphase flowback effluent stream, separating the effluent stream into secondary streams that include one or more of a solids secondary stream, a silt secondary stream, a water secondary stream, an oil secondary stream, and a gas secondary stream may allow one or more of the separated secondary streams to be sold, wherein the real-time monitoring may verify compliance with quality requirements of the customer. The measured characteristics can also be used to determine a velocity or a mass flow rate of either the substance or the entire stream.

The collected information regarding composition of the various effluent streams may demonstrate compliance with regulatory requirements as well as monitor the performance of the separation processes. Sensors comprising one or more ICEs are particularly suited for determining one or both of the concentration of substances within the flowback effluent and the individual secondary output streams and the velocities of the same streams.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the processor 810 described herein can include a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, the memory 812 may be a random-access memory (RAM), a flash memory, a read-only memory (ROM), a programmable read-only memory (PROM), an erasable read-only memory (EPROM), a register, a hard disk, a removable disk, a read-only compact disk (CD-ROM), a DVD, or any other suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a non-volatile, machine-readable medium will refer to any medium that stores instructions that, when provided to a processor for execution, configure the processor to perform a function, wherein the instructions are not lost upon removal or electrical power from the medium. Non-volatile media includes, for example, magnetically encodable media such as a floppy disk, a magnetic hard disk, a flexible magnetic tape and other like magnetic media, optically encodable media such as a CD-ROM, a rewritable CD, an optical hard disk, and other like optical media, and devices such as a PROM, an EPROM and a flash EPROM.

While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A system, comprising:
   a separator that accepts and separates a multiphase flowback effluent stream into a plurality of secondary streams;
   a first sensor assembly arranged to monitor the multiphase flowback effluent stream prior to the separator and generate a first signal corresponding to at least one characteristic of the multiphase flowback effluent stream, the first sensor assembly including a first optical computing device having an integrated computational element (ICE) that optically interacts with the multiphase flowback effluent stream;
   a second sensor assembly arranged to monitor one of the plurality of secondary streams and generate a second signal corresponding to at least one characteristic of the one of the plurality of secondary streams, the second sensor assembly including a second optical computing device having an ICE that optically interacts with the one of the plurality of secondary streams; and
   a signal processor that receives the first and second signals and determines a mass flow rate of a substance present in both the multiphase flowback effluent stream and the one of the plurality of secondary streams,
   wherein the signal processor further performs an autocorrelation operation based on the first and second signals to determine a velocity of a phase of a fluid present in both the multiphase flowback effluent stream and the one of the plurality of secondary streams.

2. The system of claim 1, wherein the plurality of secondary streams comprises at least one of a solids secondary stream, an oil secondary stream, a water secondary stream, and a gas secondary stream.

3. The system of claim 1, wherein the at least one characteristic of the multiphase flowback effluent stream comprises a concentration of the substance present in the multiphase flowback effluent stream.

4. The system of claim 1, wherein the at least one characteristic of the multiphase flowback effluent stream comprises a velocity of the multiphase flowback effluent stream.

5. The system of claim 1, wherein each ICE generates optically interacted light and the first and second optical computing devices each further include a detector arranged to receive the optically interacted light from its respective ICE and generate at least a portion of the first and second signals, respectively.

6. The system of claim 5, wherein the second optical computing device comprises a plurality of ICEs and the detector in the second optical computing device is arranged to receive optically interacted light from the plurality of ICEs and generate a corresponding plurality of individual output signals, wherein the second signal comprises at least a portion of the corresponding plurality of individual output signals.

7. The system of claim 1, where one or both of the first and second sensor assemblies includes a multiphase fluid parameter sensor that measures a velocity of the multiphase flowback effluent stream or the one of the plurality of secondary streams, respectively.

8. The system of claim 7, wherein the multiphase fluid parameter sensor comprises a plurality of ICE and at least one detector that generates at least a portion of the respective first and second signals.

9. The system of claim 7, wherein one or both of the first and second sensor assemblies further includes a densometer that measures a density of the multiphase flowback effluent stream or the one of the plurality of secondary streams, respectively, and conveys a third signal corresponding to the density to the signal processor.

10. A method, comprising:
   monitoring a multiphase flowback effluent stream with a first sensor assembly arranged prior to a separator, the first sensor assembly including a first optical computing device having an integrated computational element (ICE) that optically interacts with the multiphase flowback effluent stream;
   generating a first signal corresponding to at least one characteristic of the multiphase flowback effluent stream with the first sensor assembly;
   separating the multiphase flowback effluent stream with the separator into a plurality of secondary streams;
   monitoring one of the plurality of secondary streams with a second sensor assembly, the second sensor assembly including a second optical computing device having an ICE that optically interacts with the one of the plurality of secondary streams;
   generating a second signal corresponding to at least one characteristic of the one of the plurality of secondary streams;
   receiving the first and second signals with a signal processor;
   determining with the signal processor a mass flow rate of a substance present in both the multiphase flowback effluent stream and the one of the plurality of secondary streams based on the first and second signals; and performing an autocorrelation operation with the signal processor based on the first and second signals and thereby determining a velocity of a phase of a fluid present in both the multiphase flowback effluent stream and the one of the plurality of secondary streams.

11. The method of claim 10, wherein separating the multiphase flowback effluent stream comprises at least one of:
generating a solids secondary stream;
generating an oil secondary stream;
generating a water secondary stream; and
generating a gas secondary stream.

12. The method of claim 10, wherein the at least one characteristic of the multiphase flowback effluent stream comprises a concentration of the substance of the multiphase flowback effluent stream, and wherein receiving the first and second signals with the signal processor further comprises determining the concentration of the substance of the multiphase flowback effluent stream with the signal processor as based on the first and second signals.

13. The method of claim 10, wherein the at least one characteristic of the multiphase flowback effluent stream comprises a velocity of the multiphase flowback effluent stream, and wherein receiving the first and second signals with the signal processor further comprises determining the velocity of the substance of the multiphase flowback effluent stream with the signal processor as based on the first and second signals.

14. The method of claim 10, wherein the ICE in the first optical computing device generates first optically interacted light and the ICE in the second optical computing device generates second optically interacted light, the method further comprising:
receiving the first optically interacted light with a first detector included in the first optical computing device;
generating at least a portion of the first signal with the first detector;
receiving the second optically interacted light with a second detector included in the second optical computing device; and
generating at least a portion of the second signal with the second detector.

15. The method of claim 14, wherein the second optical computing device comprises a plurality of ICEs, the method further comprising:
receiving optically interacted light from the plurality of ICEs with the second detector; and
generating a plurality of individual output signals with the second detector corresponding to the optically interacted light from the plurality of ICEs, wherein the second signal comprises at least a portion of the plurality of individual output signals.

16. The method of claim 10, further comprising measuring a velocity of the multiphase flowback effluent stream with a multiphase fluid parameter sensor included in the first sensor assembly.

17. The method of claim 10, further comprising measuring a velocity of the one of the plurality of secondary streams with a multiphase fluid parameter sensor included in the second sensor assembly.

18. The method of claim 17, wherein the multiphase fluid parameter sensor comprises a plurality of ICEs, the method further comprising:
receiving optically interacted light from the plurality of ICEs with at least one detector included in the second sensor assembly; and
generating at least a portion of the second signal with the at least one detector corresponding to the optically interacted light from the plurality of ICEs.

19. The method of claim 10, further comprising:
measuring a density of the multiphase flowback effluent stream with a densometer included in the first sensor assembly;
generating a third signal with the densometer corresponding to the density of the multiphase flowback effluent stream; and
conveying the third signal to the signal processor.

20. The method of claim 10, further comprising:
measuring a density of the one of the plurality of secondary streams with a densometer included in the second sensor assembly;
generating a third signal with the densometer corresponding to the density of the one of the plurality of secondary streams; and
conveying the third signal to the signal processor.

* * * * *